United States Patent [19]
Law et al.

[11] Patent Number: 4,933,121
[45] Date of Patent: Jun. 12, 1990

[54] PROCESS FOR FORMING LIPOSOMES

[75] Inventors: Say-Jong Law, Westwood; Uri Piran, Sharon, both of Mass.

[73] Assignee: Ciba Corning Diagnostics Corp., Medfield, Mass.

[21] Appl. No.: 224,033

[22] Filed: Jul. 25, 1988

Related U.S. Application Data

[63] Continuation of Ser. No. 940,519, Dec. 10, 1986, abandoned.

[51] Int. Cl.⁵ ............... A61K 9/66; A61K 37/22; A61K 37/48; B01J 13/02
[52] U.S. Cl. .................... 264/4.3; 264/4.1; 264/4.6; 424/94.3; 424/450; 425/5; 436/829
[58] Field of Search ............... 264/4.1, 4.3; 424/450; 436/829

[56] References Cited

U.S. PATENT DOCUMENTS

| | | | |
|---|---|---|---|
| 4,263,428 | 4/1981 | Apple et al. | 536/6.4 |
| 4,448,765 | 5/1984 | Ash et al. | 424/450 |
| 4,529,561 | 7/1985 | Hunt et al. | 436/829 X |
| 4,564,599 | 1/1986 | Janoff et al. | 424/450 X |
| 4,605,630 | 8/1986 | Kung et al. | 428/402.2 X |
| 4,619,795 | 10/1986 | Cohen | 428/402.2 X |

OTHER PUBLICATIONS

Szoka, Jr. et al.: "Comparative Properties and Methods of Preparation of Lipid Vesicles (Liposomes)", *Ann. Rev. Biophys. Bioeng.* 9: 467–508 (1980).

*Primary Examiner*—Richard D. Lovering
*Attorney, Agent, or Firm*—Nicholas I. Slepchuk; William G. Gosz

[57] ABSTRACT

The present invention relates to a process for forming stable, uniform unilamellar or oligolamellar liposomes which encapsulate a macromolecule. However, unlike prior processes, the present method maintains a temperature below the phase transition temperature of the lipid used to make the liposome both during the hydration of the lipid and, if used, during an extrusion step. In addition, the liposome is formed and the macromolecule encapsulated in a low ionic strength solution, then they are dialyzed against a high ionic strength solution.

7 Claims, 1 Drawing Sheet

PROCESS FOR FORMING LIPOSOMES

This application is a continuation of U.S. Ser. No. 940,519, filed Dec. 10, 1986, now abandoned.

TECHNICAL FIELD

The present invention relates to a process for forming stable, uniform unilamellar or oligolamellar liposomes which encapsulate a macromolecule. However, unlike prior processes, the present method maintains a temperature below the phase transition temperature of the lipid used to make the liposome both during the hydration of the lipid and, if used, during an extrusion step. In addition, the liposome is formed and the macromolecule encapsulated in a low ionic strength solution, then they are dialyzed against a high ionic strength solution.

BACKGROUND ART

The production of a liposome which encapsulates a macromolecule by high-pressure extrusion process is known to the art. An article by Peter I. Lelkes discloses the use of a French press to form various forms of encapsulating liposomes, for example, a homogeneous population of small unilamellar vesicles, i.e. liposomes, or a mixture of oligolamellar and multilamellar vesicles, all referred to as FPVs. See *Liposome Technology*, Gregory Gregoriadis (ed.), Vol. 1, Chap. 5, (1984) pp. 51–65. Essentially, an aqueous suspension of a hydrated phospholipid encapsulating a macromolecule is extruded through an orifice at pressures of between 5,000 and 20,000 psi. If the extrusion is done at a temperature above the phase transition temperature, then small unilamellar liposomes result. However, if not, then a mixture of oligolamellar and multilamellar liposomes are formed.

One of the uses for liposome with encapsulated macromolecules is as a label for diagnostic assays. For example, in U.S. Pat. No. 4,342,826, issued to Francis X. Cole, a liposome is filled with an enzyme and is conjugated to an antibody to form a labelled reactant in a homogeneous immunoassay. After an immunocomplex is formed between the antibody and the corresponding antigen, a signal is generated when complement, a specific mixture of serum proteins, fixes to the surface of the immunocomplex and creates holes in the lipid bilayer wall of the liposome and allow substrate on the outside of the liposome to be exposed to the enzyme on the inside. In a preferred embodiment the substrate undergoes a colorimetric change upon exposure. An important limitation to this assay is the type of liposome used to encapsulate the enzyme. Multilamellar liposomes have upwards of ten phospholipid bilayers surrounding the enzyme, an undesirable barrier to complement. Only unilamellar or oligolamellar liposomes are suitable for use in immunoassays.

DISCLOSURE OF THE INVENTION

The present process is for forming stable, uniform unilamellar or oligolamellar liposomes which encapsulate a macromolecule. The artisan makes a lipid film out of known materials and by conventional means. However, in the present process, when a lipid suspension is formed by hydrating the film in the presence of the macromolecule to be encapsulated, the temperature for hydration is below the lipid phase-transition temperature, but above ambient temperature. This range of temperatures is maintained even if one processes the liposomes by an extrusion process.

Consistent liposome size is achieved by passing the liposome suspension through conventional membrane extrusion means. However, unlike previous methods, in a preferred form of the present method, an extrusion step can be performed at low pressures, i.e. less than 500 psi. The result is unilamellar or oligolamellar liposomes which, when exposed to complement, can retain an entrapped macromolecule but allow smaller molecules to enter the lipid bilayer wall of the liposome. Moreover, by avoiding the use of high pressures and temperatures, the present invention provides a greater safety factor in manufacturing, lower cost of manufacturing, and the end to problems of membrane clogging.

BRIEF DESCRIPTION OF DRAWING

The sole figure is a schematic diagram of the present process.

MODES OF THE INVENTION

Figure 1:
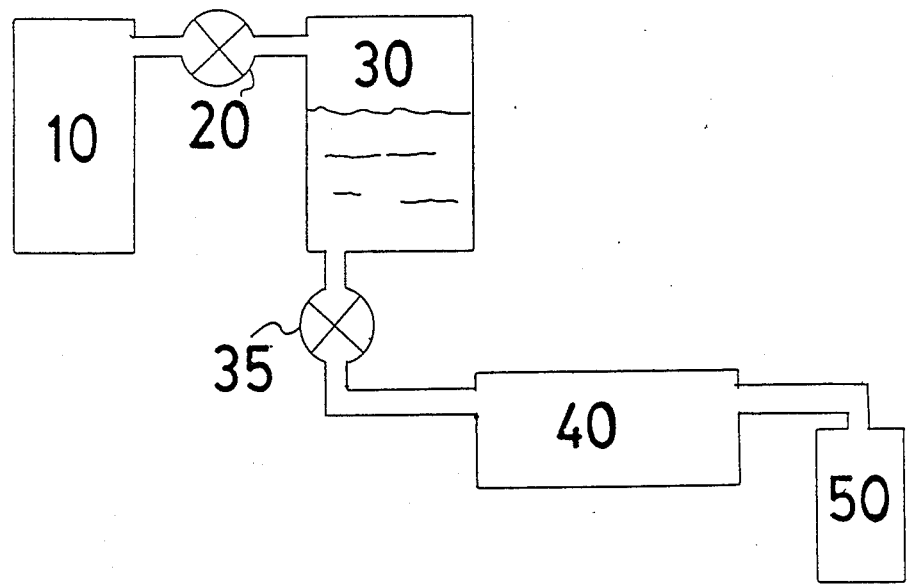

In a preferred mode, the process comprises five steps; namely, lipid film preparation, lipid film hydration, liposome dialysis, liposome extrusion, and finally, liposome washing. These steps are described below in detail with reference to the sole Figure to explain an extrusion device suitable for the present process.

LIPID FILM PREPARATION

Preferably, a phospholipid with fully saturated long-chain fatty acids such as dipalmitoyl phosphatidylcholine (DPPC)(25mg) was mixed with 13.5mg of cholesterol and 2.3mg of dipalmitoyl phosphatidylglycerol (DPPG), then dissolved in chloroform. The resulting solution was transferred to a substantially flat-bottomed evaporating dish having a 4cm diameter. After evaporating the chloroform in vacuo by known methods, a homogeneous lipid film having a net negative charge deposits on the bottom of the dish.

LIPID FILM HYDRATION

The above lipid film was hydrated by adding water onto the lipid film in the dish, and, again, if one desired to make a reagent for the Cole assay, water containing the enzyme glucose-6-phosphate dehydrogenase (G-6-PDH). For example, 12mg of G-6-PDH is diluted into 2ml of a 2% aqueous glycerol solution having 0.25 mM of EDTA. The dish was swirled in an orbital manner in a shaker bath at 150rpm at 38° C for 20 minutes. (The phase transition temperature for the phospholipids is about 42° C.)

As a result, liposomes were formed which encapsulated G-6-PDH. It should be noted that complete hydration of the lipid film is desired. This event is based on the area of the lipid film, the temperature, the speed of shaking, and the ratio of lipid-to-enzyme volume. Thus, the time should be adjusted as these other variables are changed.

LIPOSOME DIALYSIS

It has been known that if one hydrates the lipid film with an aqueous solution of low ionic strength, i.e., one containing less than 10mM of ionic species, then more macromolecule can be encapsulated than if one had used a high ionic strength solution. However, liposomes which encapsulate macromolecules that are formed in low ionic solutions have been found not to be stable. They lose their activity through the inability of the macromolecule to tolerate low ionic strengths, especially under heat stress conditions. The present process enables both greater encapsulation and stability by forming the liposomes in low ionic strength solutions, then dialyzing the liposomes against high ionic strength solutions.

In order to increase the ability of the macromolecule encapsulated liposomes to withstand heat stress and remain active, they were dialyzed against a high ionic strength buffer, which contains greater than 100mM of ionic species, preferably having TRIS and azide ion. This novel method of first hydrating a lipid film in low ionic strength solutions followed by dialysis in high ionic strength solutions permitted large scale production of liposomes. More particularly, the liposomes were dialyzed two to three times over a two-day period at 4° C against fresh solutions of a pH 7.8 solution containing 0.1M TRIS, 0.03M NaCl, 0.25mM EDTA, and 0.01% sodium azide.

One can use conventional dialysis means such as dialysis bags or hollow fibers. If a macromolecule is encapsulated, one should dialyze with a membrane having a porosity sufficient to retain any free macromolecule surrounding the liposome. Alternatively, one can perform this dialysis step after the liposome extrusion described below.

LIPOSOME EXTRUSION

During hydration of the lipid film, liposomes were formed having diameters ranging from 0.025um to 5um. The size distribution range was homogenized by repeatedly passing the mixture through an extruder equipped with a polycarbonate membranes of successively smaller porosity. For example, when 0.6um liposomes were desired, the mixture was passed through a series of 3.0, 2.0, 1.0 and finally twice through 0.6um membranes.

The diagram in the Figure illustrates a suitable extruder. A pressurizing means (10) comprises a readily available compressed nitrogen tank. Nitrogen gas is preferred because it cannot oxidize either the liposome or the encapsulated macromolecule. The gas is passed into a valving means (20) which limits the pressure to under 500 psi, and more preferably, under 100 psi. After being pressure-regulated by the valving means, the gas is passed into a reservoir (30) that is preloaded with the liposome mixture. The pressure forces the liposomes through a valve (35) and into an extruder (40) comprised of a series of polycarbonate membranes which limit the final size to the desired diameter, which are collected in a vessel (50). Between the reservoir and the extrusion membranes is a means which regulates the temperature as described above.

For the above DPPC-based liposomes, the temperature was maintained at 31° C and the pressure was less than 30 psi. The complete extrusion through a series of five membranes took about 90 minutes for 225ml of liposome suspension made from 3000mg of total dry lipid. Unilamellar or oligolamellar liposomes were produced having a 0.6um diameter and encapsulated G-6-PDH.

LIPOSOME WASHING

Finally, extruded product was washed to remove any unencapsulated enzyme. This was done by ultracentrifuging (35,000 rpm) the liposomes into a pellet, pipetting the resultant supernatant, and resuspending the liposome pellet, the entire cycle being repeated three to four times.

When the finished product was tested according to the method of the Cole patent, the suitability of the present process to create liposomes was confirmed.

It should be apparent to one having ordinary skill in the art that many variations are possible without departing from the spirit and scope of the invention.

We claim:

1. A process for forming unilamellar or oligolamellar liposomes which encapsulate a macromolecule comprising:
   a. forming a lipid film which lipid film comprises a phospholipid with a phase-transition temperature greater than about 31° C; and
   b. hydrating the lipid film in the presence of a macromolecule to be encapsulated at a temperature between about 31° C and 42° C, said temperature of hydration being below the phase-transition temperature of the phospholipid, to form a liposome suspension, and wherein the lipsome suspension is extruded so as to form liposomes having a desired size, said extrusion occurring at a temperature between 37° C and 42° C, said temperature of extrusion being below the phase-transition temperature of the phospholipid of the liposomes.

2. A process as recited in claim 1, wherein the phospholipid has fully saturated fatty acid radical substituents.

3. The process as recited in claim 1, wherein the phospholipid comprises a mixture of dipalmitoyl phosphatidylcholine, dipalmitoyl phosphatidylglycerol and cholesterol.

4. A process as recited in claim 1, wherein the macromolecule is a protein.

5. A process as recited in claim 4, wherein the protein is an enzyme.

6. The process as recited in claim 1, wherein the liposome is extruded through a membrane means at less than 500 psi, the membrane means having at least two sequentially smaller porosity membranes, the final membrane having a porosity equal to the desired size of the liposome.

7. The process as recited in claim 1, wherein the extrusion step is performed at pressure less than 200 psi.

* * * * *